(12) United States Patent
Huang

(10) Patent No.: US 8,555,952 B2
(45) Date of Patent: Oct. 15, 2013

(54) HEAT SINK WITH FINS HAVING ANGLED FOOT PORTION

(76) Inventor: Tsung-Hsien Huang, I-Lan Hsien (TW)

( * ) Notice: Subject to any disclaimer, the term of this patent is extended or adjusted under 35 U.S.C. 154(b) by 448 days.

(21) Appl. No.: 12/480,461

(22) Filed: Jun. 8, 2009

(65) Prior Publication Data

US 2010/0263850 A1   Oct. 21, 2010

(30) Foreign Application Priority Data

Apr. 17, 2009   (TW) .............................. 98206415 U

(51) Int. Cl.
*F28F 7/00* (2006.01)
*H05K 7/20* (2006.01)

(52) U.S. Cl.
USPC ........................................ 165/80.3; 361/700

(58) Field of Classification Search
USPC ........................................ 165/80.3; 361/700
See application file for complete search history.

(56) References Cited

U.S. PATENT DOCUMENTS

| | | | | |
|---|---|---|---|---|
| 851,977 A * | 4/1907 | Bigsby et al. | ................. | 165/183 |
| 5,014,776 A * | 5/1991 | Hess | .............. | 165/185 |
| 5,038,858 A * | 8/1991 | Jordan et al. | .................. | 165/185 |
| 5,542,176 A * | 8/1996 | Serizawa et al. | ........... | 29/890.03 |
| 6,742,581 B2 * | 6/2004 | Mochizuki et al. | ........... | 165/185 |
| 6,754,078 B1 * | 6/2004 | Chen | .............. | 361/709 |
| 6,758,262 B2 * | 7/2004 | Kawabata et al. | ........... | 165/80.3 |
| 6,776,224 B1 * | 8/2004 | Chen | ............................. | 165/80.3 |
| 7,286,352 B2 * | 10/2007 | Curtis et al. | .................. | 361/697 |
| 7,600,558 B2 * | 10/2009 | Chen | ............................. | 165/80.3 |
| 7,661,192 B2 * | 2/2010 | Fujimori et al. | ......... | 29/890.046 |
| 8,413,713 B2 * | 4/2013 | Huang | ........................ | 165/80.3 |
| 2002/0070005 A1 * | 6/2002 | Kawabata et al. | ........... | 165/80.3 |
| 2006/0070721 A1 * | 4/2006 | Chen | ............................. | 165/80.3 |
| 2006/0181848 A1 * | 8/2006 | Kiley et al. | .................... | 361/697 |
| 2007/0051495 A1 * | 3/2007 | Hsiao | ............................ | 165/80.3 |
| 2007/0221369 A1 * | 9/2007 | Getz et al. | ..................... | 165/185 |
| 2008/0047693 A1 * | 2/2008 | Chen | ........................ | 165/104.33 |
| 2008/0060793 A1 * | 3/2008 | Huang | ..................... | 165/104.33 |
| 2009/0025906 A1 * | 1/2009 | Huang | ........................ | 165/80.3 |
| 2009/0032221 A1 * | 2/2009 | Huang | ........................ | 165/80.3 |
| 2009/0194255 A1 * | 8/2009 | Huang | ........................ | 165/80.3 |

FOREIGN PATENT DOCUMENTS

CN    1655344 A  *  8/2005

OTHER PUBLICATIONS

English Abstract of CN1655344A, 1 page.*

* cited by examiner

*Primary Examiner* — Brandon M Rosati
(74) *Attorney, Agent, or Firm* — Pai Patent & Trademark Law Firm; Chao-Chang David Pai

(57) ABSTRACT

A heat sink includes a base panel having parallel channels located on the top wall, first ribs protruding from the top wall and respectively extending along one side of each channel and second ribs protruding from the top wall and respectively extending along the other side of each channel, and radiation fins respectively mounted in the channels of the base panel and supported on the second ribs in vertical positions, each radiation fin having an angled foot portion, which is inserted into one channel and secured thereto by the associated first rib upon deformation of the associated first rib by an external force.

5 Claims, 8 Drawing Sheets

HEAT SINK WITH FINS HAVING ANGLED FOOT PORTION

BACKGROUND OF THE INVENTION (a) Field of the Invention

The present invention relates to heat sinks and more particularly to such a heat sink that has the radiation fins fastened to the base panel by means of press-fit engagement.

(b) Description of the Prior Art

Many conventional heat sinks have the radiation fins bonded to the base panel by means of a soldering technique. There are heat sinks in which the base panel has channels for the mounting of radiation fins. A similar design is disclosed in U.S. Pat. No. 6,571,859 in which plate-like cooling ribs, projecting from a base plate at intervals and approximately parallel to each other, protrude with a connection strip into the base plate in which they are cast. U.S. Pat. No. 5,014,776 discloses a heat emitting unit in which a number of parallel, flat ribs are attached to at least one side of the main body and projecting from the main body. The ribs pressed into place through deformation of the intermediary ridges after insertion into channels on the main body.

Employing a soldering technique to bond radiation fins to a base panel is not environmentally friendly. Further, U.S. Pat. No. 5,014,776 simply has the parallel, flat ribs pressed into place through deformation of the intermediary ridges after insertion into channels on the main body. This method simply provides a two-point clamping force to secure each flat rib to the associated channel. If the parallel, flat ribs are not accurately inserted into the channels or a vibration occurs when the parallel, flat ribs are pressed into place through deformation of the intermediary ridges after insertion into channels, the flat ribs may not be all kept in close contact with the bottom edges of the channels to show an equal height. If the flat ribs do not show an equal height after installation, the heat emitting unit will be regarded as a defective product, and the flat ribs may vibrate or fall from the main body.

SUMMARY OF THE INVENTION

The present invention has been accomplished under the circumstances in view. A heat sink according to the present invention includes a base panel and a plurality of radiation fins fastened to the base panel. The base panel has a top wall, a plurality of channels located on the top wall and arranged in parallel, and a plurality of first ribs protruding from the top wall and respectively extending along one side of each channel. Each radiation fin has an angled foot portion, which is inserted into one channel and secured thereto by the associated first rib, which is deformed by a stamping mold after insertion of the respective radiation fin into the respective channel. When assembled, the radiation fins are firmly secured to the channels of the base panel and kept in flush.

Further, the angle of the angled foot portions of the radiation fins can be 90-degrees, greater than 90-degrees, or smaller than 90-degrees.

The base panel further comprises a plurality of second ribs protruding from the top wall and respectively extending along an opposite side of each channel for supporting the radiation fins in vertical.

Further, the angled foot portion of each radiation fin can have a fold-up structure. The angle of the fold-up structure of the angled foot portion can be 90-degrees, greater than 90-degrees, or smaller than 90-degrees.

Further, each radiation fin can also include at least one retaining lug protruding from the top edge thereof for fastening.

Further, heat pipes may be installed in the radiation fin and kept in close contact with the top wall of the base panel for transferring heat energy from the base panel to the radiation fins for quick dissipation into surrounding air.

Further, heat pipes may be installed in the radiation fins and partially embedded in the bottom side of the base panel in a flush manner.

DETAILED DESCRIPTION OF THE PREFERRED EMBODIMENTS

Figure 1:
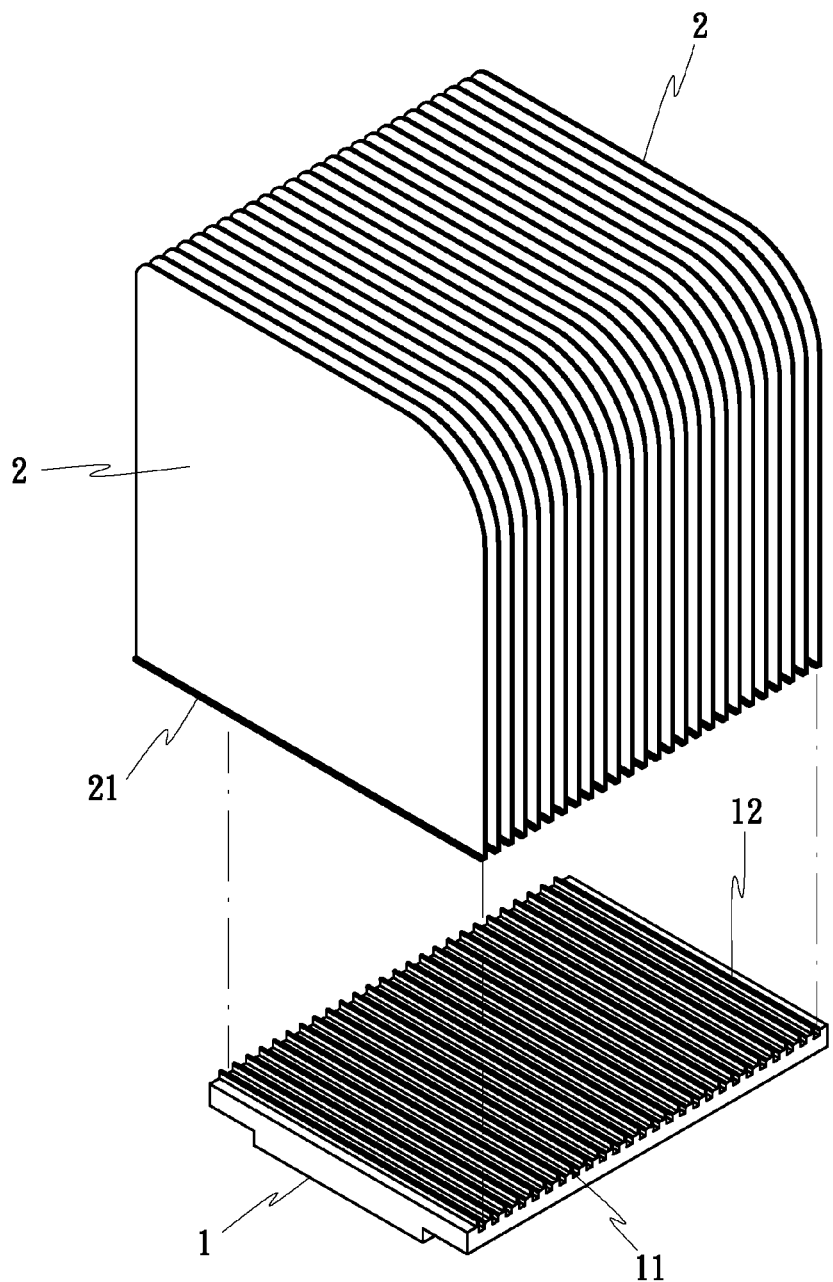
FIG. 1 is an exploded view of a heat sink in accordance with a first embodiment of the present invention.
Figure 2:
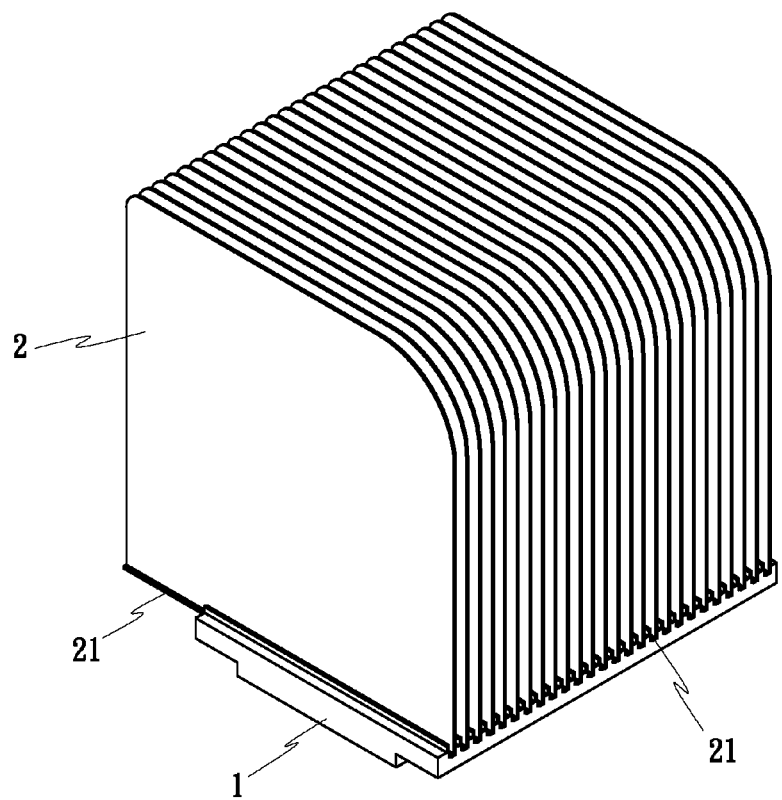
FIG. 2 is an oblique elevation of the heat sink in accordance with the first embodiment of the present invention.

Referring to FIGS. 1 and 2, a heat sink in accordance with a first embodiment of the present invention is shown comprising a base panel 1 and a number of radiation fins 2.

Figure 3:
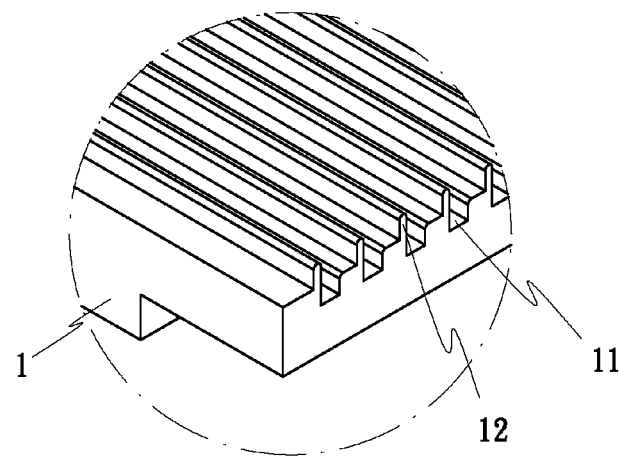
FIG. 3 is an enlarged view of a part of FIG. 1, showing the structure of the base panel.

The base panel 1 has parallel channels 11 located on the top wall and a first rib 12 protruding from the top wall and extending along one side of each channel 11 (see FIG. 3).

The radiation fins 2 each have an angled foot portion 21 insertable into the channels 11 of the base panel 1 respectively.

Figure 4:
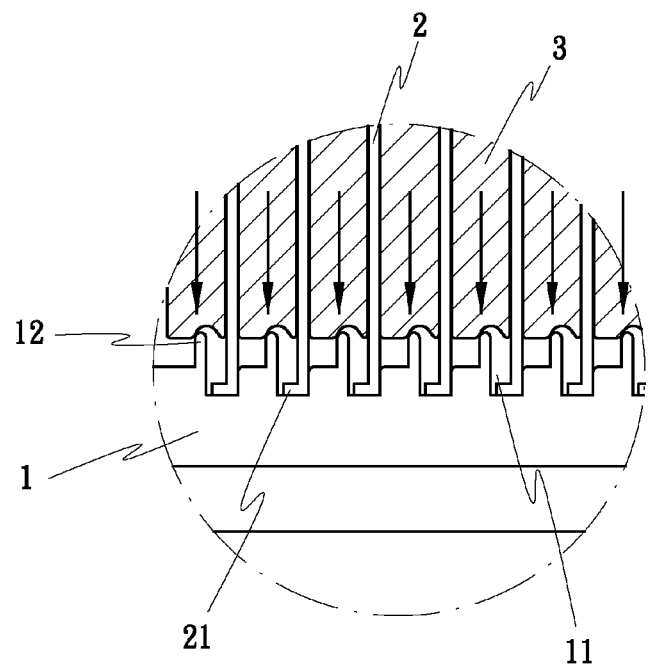
FIG. 4 is a schematic drawing showing the installation of the radiation fins in the base panel having first ribs in accordance with the first embodiment of the present invention.
Figure 5:
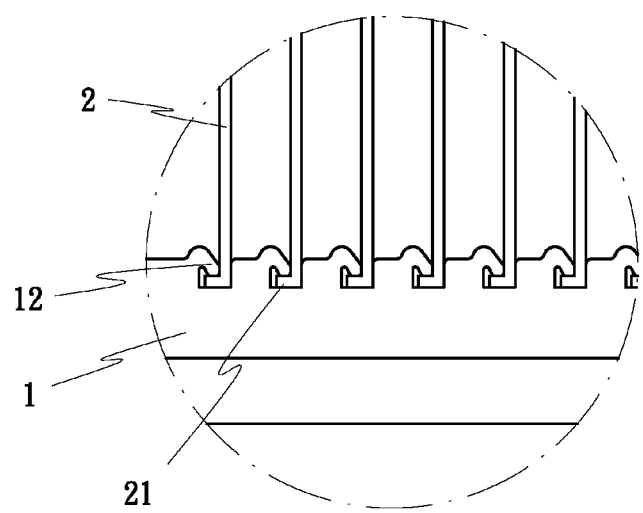
FIG. 5 corresponds to FIG. 4, showing the first ribs of the base panel respectively forced into engagement with the angled foot portions of the radiation fins after installation.

During the assembly process of the heat sink, the angled foot portions 21 of the radiation fins 2 are inserted into the channels 11 of the base panel 1 respectively, and then a stamping mold 3 is used (see FIG. 4) to stamp the first ribs 12 of the base panel 1, deforming the first ribs 12 and forcing the deformed first ribs 12 into tight engagement with the angled foot portions 21 of the radiation fins 2 in the channels 11 of the base panel 1 respectively (see FIG. 5). When assembled, the radiation fins 2 are firmly secured to the base panel 1, and kept in parallel in a flush manner (see FIG. 2).

Figure 6:
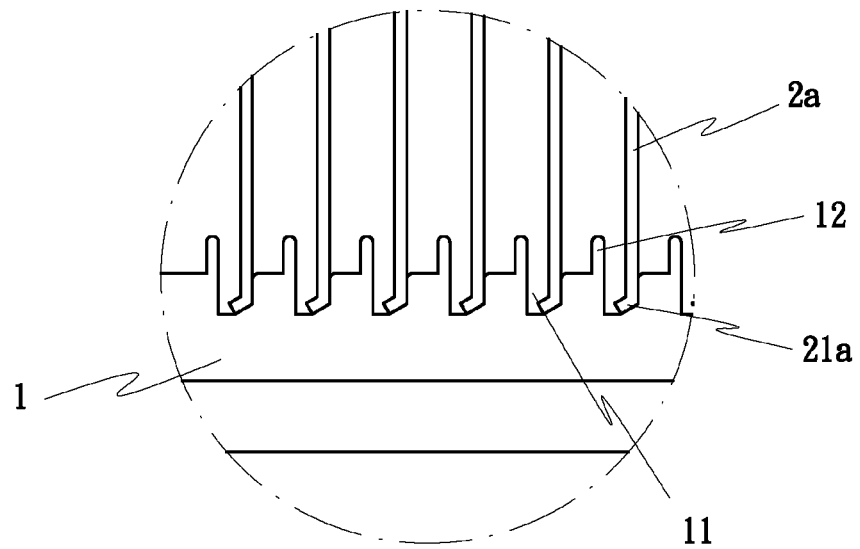
FIG. 6 is a schematic drawing of a part of a heat sink in accordance with a second embodiment of the present invention, wherein the angle of the angled foot portions of the radiation fins is an obtuse angle.
Figure 7:
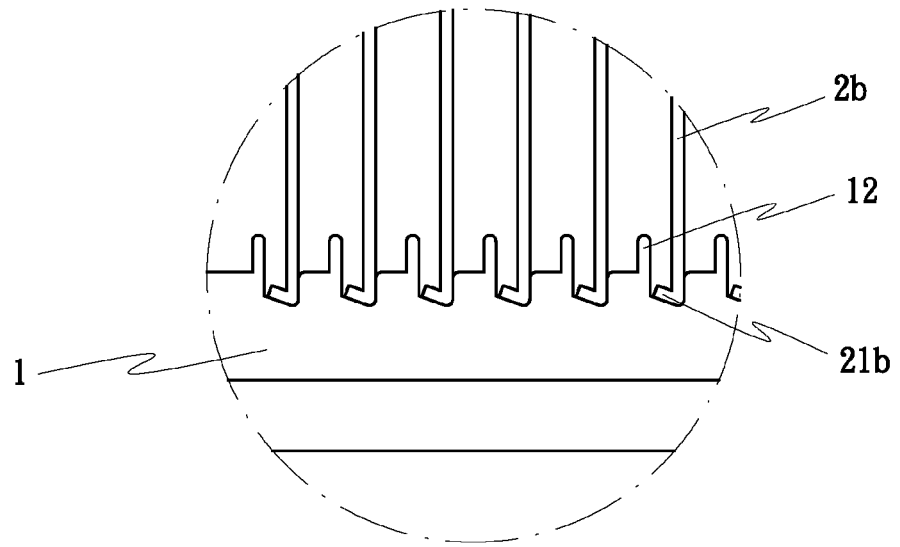
FIG. 7 is a schematic drawing of a part of a heat sink in accordance with a third embodiment of the present invention, wherein the angle of the angled foot portions of the radiation fins is an acute angle.

Referring to FIG. 5, the angle of the angled foot portions 21 of the radiation fins 2 in accordance with the first embodiment of the present invention is 90-degrees. According to a second embodiment of the present invention as shown in FIG. 6, the angle of the angled foot portions 21a of the radiation fins 2a is an obtuse angle (i.e. over 90-degrees). According to a third embodiment of the present invention, as shown in FIG. 7, the angle of the angled foot portions 21b of the radiation fins 2b is an acute angle (i.e. smaller than 90-degrees). Therefore, the angled foot portions 21, 21b, 21b of the radiation fins 2, 2a, 2b can be a right angle, an obtuse angle or an acute angle. In consequence, the foot portions of the channels 11 of the base panel 1 are configured subject to the angle of the angled foot portions 21, 21b, 21b of the radiation fins 2, 2a, 2b, respectively.

Figure 8:
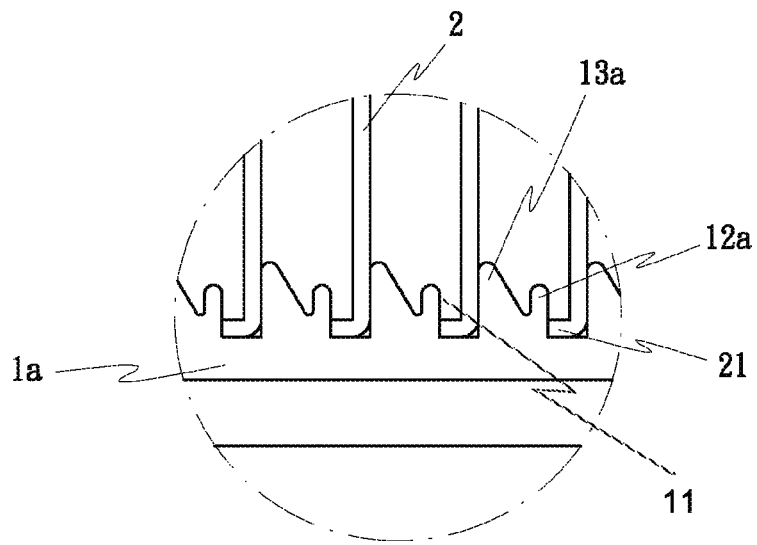
FIG. 8 is a schematic drawing showing the installation of the radiation fins in the base panel having both first ribs and second ribs in accordance with a third embodiment of the present invention.
Figure 9:
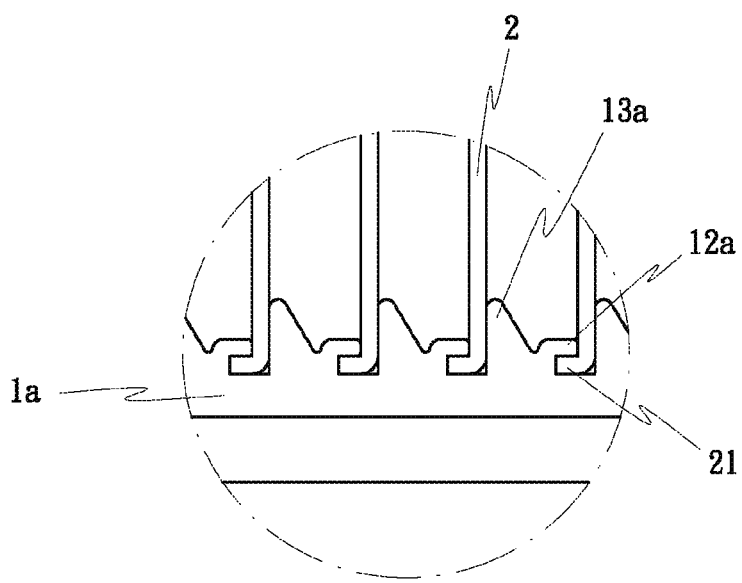
FIG. 9 corresponds to FIG. 8, showing the first ribs of the base panel respectively forced into engagement with the angled foot portions of the radiation fins after installation.

According to the third embodiment shown in FIG. 8, the base panel 1a has a first rib 12a protruding from the top wall and extending along one side of each channel 11, and a second rib 13a protruding from the top wall and extending along the other side of each channel 11. After insertion of the radiation fins 2 into the channels 11 of the base panel 1 (see FIG. 8) and secured thereto by the first ribs 12a (see FIG. 9), the second ribs 13a give a support to the radiation fins 2 respectively (see FIG. 9), thereby holding the radiation fins 2 firmly in vertical positions.

Figure 10:
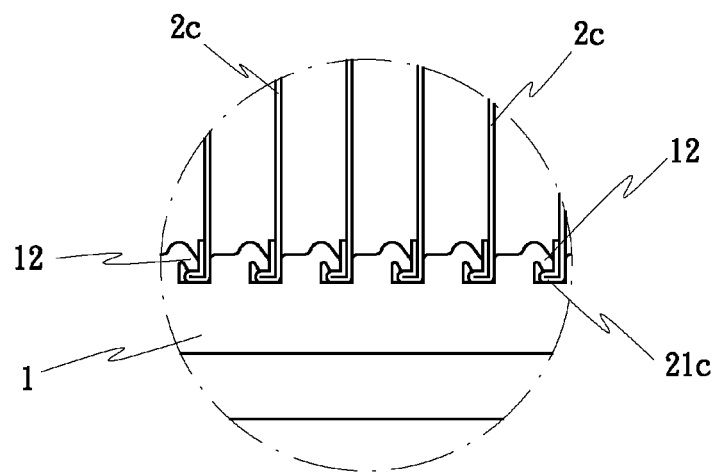
FIG. 10 is a schematic drawing of a part of a heat sink in accordance with a fourth embodiment of the present invention, wherein the foot portions of the radiation fins are folded up and angled.
Figure 11:
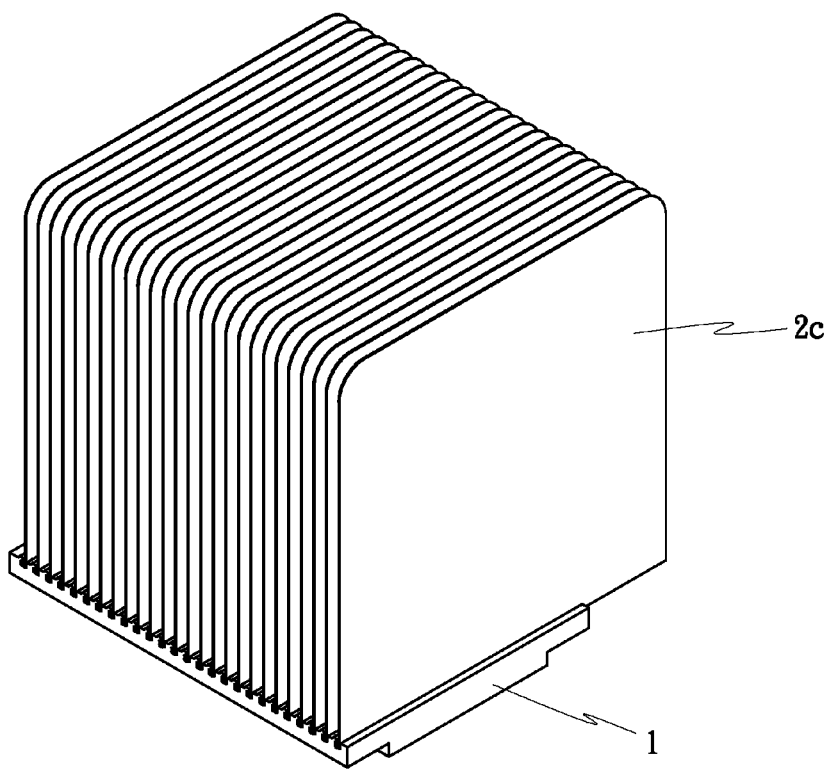
FIG. 11 is an oblique elevation of the heat sink in accordance with the fourth embodiment of the present invention.

FIGS. 10 and 11 show a heat sink in accordance with a fourth embodiment of the present invention. According to this fourth embodiment, the radiation fins 2c are relatively thinner when compared to the aforesaid various embodiments, each having a foot portion 21c folded up and angled. The angle of the folded-up and angled foot portion 21c can be equal to, greater than or smaller than 90-degrees, in order to fit the foot portions of the channels 11 of the base panel 1.

Figure 12:
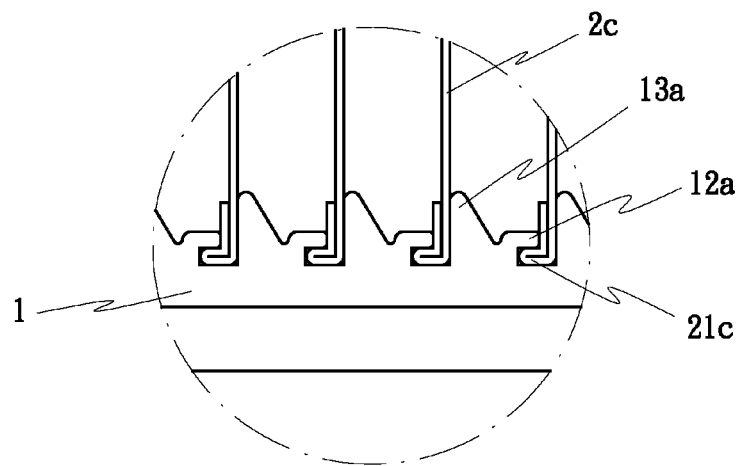
FIG. 12 is a schematic drawing of a part of a heat sink in accordance with a fifth embodiment of the present invention, showing the radiation fins supported on the second ribs of the base panel and the first ribs of the base panel respectively forced into engagement with the folded-up angled foot portions of the radiation fins.

FIG. 12 is a schematic drawing of a part of a heat sink in accordance with a fifth embodiment of the present invention. This fifth embodiment is substantially similar to the aforesaid fourth embodiment with the exception that the base panel 1 according to this fifth embodiment has second ribs 13a disposed opposite to the first ribs 12a to support the radiation fins 2c in vertical positions.

Figure 13:
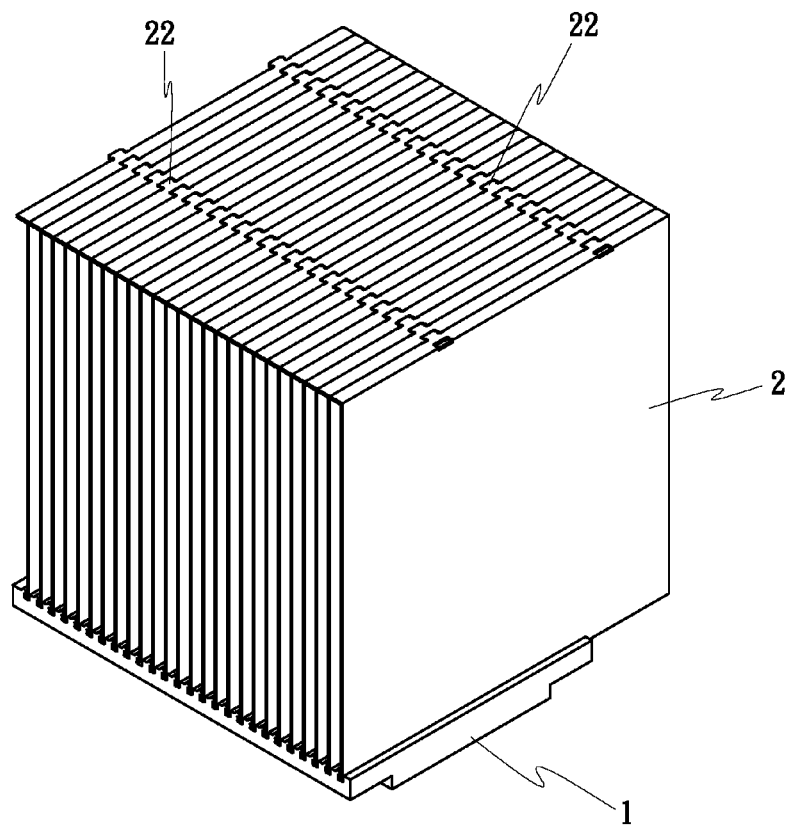
FIG. 13 is an oblique elevation of a heat sink in accordance with a sixth embodiment of the present invention.

FIG. 13 is an oblique elevation of a heat sink in accordance with a sixth embodiment of the present invention. According to this sixth embodiment, each radiation fin 2 has a plurality of retaining lugs 22 protruding from the top edge thereof. By means of connecting the retaining lugs 22 of one radiation fin 2 to the retaining lugs 22 of an adjacent radiation fin 2, the top edges of the radiation fins 2 are firmly secured together.

Figure 14:
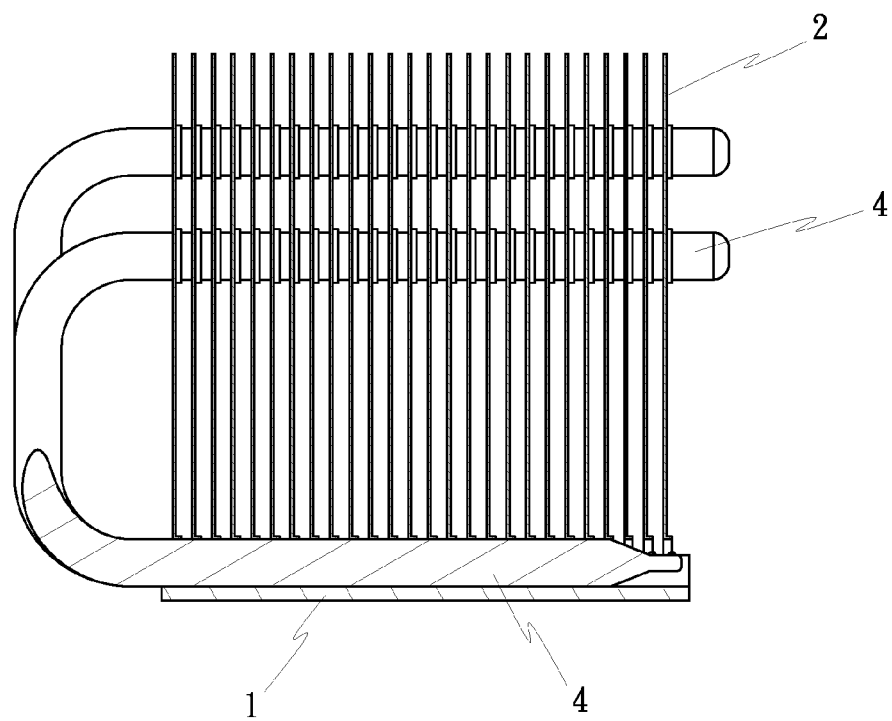
FIG. 14 is a schematic side view of a heat sink in accordance with a seventh embodiment of the present invention.

FIG. 14 is a schematic side view of a heat sink in accordance with a seventh embodiment of the present invention. According to this seventh embodiment, heat pipes 4 are installed through the radiation fins 2 and kept in close contact with the top wall of the base panel 1 for quick transfer of heat energy from the base panel 1 to the radiation fins 2 for quick dissipation into the surrounding air.

Figure 15:
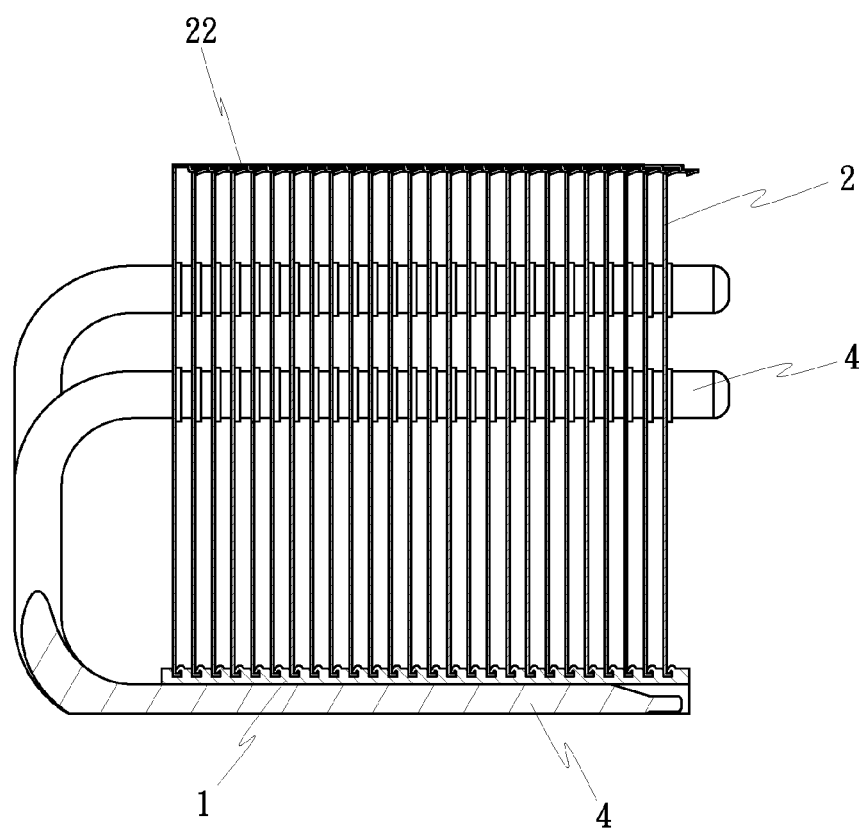
FIG. 15 is a schematic side view of a heat sink in accordance with an eighth embodiment of the present invention.

FIG. 15 is a schematic side view of a heat sink in accordance with an eighth embodiment of the present invention. This eighth embodiment is substantially similar to the aforesaid seventh embodiment with the exception that the heat pipes 4 each have one end mounted in the bottom side of the base panel 1 and kept in flush with the bottom wall of the base panel 1.

Prototypes of heat sink have been constructed with the features of FIGS. 1~15. The heat sink functions smoothly to provide all of the features disclosed earlier.

Although particular embodiments of the invention have been described in detail for purposes of illustration, various modifications and enhancements may be made without departing from the spirit and scope of the invention. Accordingly, the invention is not to be limited except as by the appended claims.

What is claimed is:

1. Parts for a heat sink, comprising:
   a base panel, said base panel having a top wall, a plurality of vertical channels, each having a first vertical side, a second vertical side, a horizontal bottom side, and a uniform width between the first vertical side and the second vertical side, located on said top wall and arranged in parallel, and a plurality of first ribs vertically protruding from said top wall and respectively extending along the first vertical side of said channels; and
   a plurality of radiation fins, each having a right-angled foot portion including a vertical portion and a horizontal portion extending horizontally from a bottom end of the vertical portion, the horizontal portion having a top side and a bottom side parallel to the top side, wherein the vertical portion and the horizontal portion are of substantially equal thickness, and when each radiation fin is respectively inserted into one said channel, the bottom side of the horizontal portion of the right-angled foot entirely rests on the bottom side of said channel,
   wherein the uniform width of each said channel is the same as or larger than the overall horizontal width of the right-angled foot portion of the associated radiation fin, allowing the associated radiation fin to be inserted vertically from above into the channel without obstruction; and
   said base panel further comprises a plurality of second ribs vertically protruding from said top wall, wherein the second ribs respectively extend along the second vertical sides of said channels opposite to said first ribs, wherein the second ribs are taller than the first ribs as measured from the bottom of said channels to a respective highest point thereof for keeping the radiation fins vertical, and each second rib has a downward-inclined side which intersects with a lower edge of one of the first ribs;
   whereby each radiation fin is capable of being secured to the associated channel by deforming the associated first rib to be laid over the entire horizontal portion of the angled foot portion.

2. The parts for a heat sink as claimed in claim 1, wherein the angled foot portion of each said radiation fin has a folded-up structure.

3. The parts for a heat sink as claimed in claim 1, wherein each said radiation fin has at least one retaining lug protruding from a top edge thereof for fastening.

4. The parts for a heat sink as claimed in claim 1, further comprising at least one heat pipe for passing through said radiation fins and kept in close contact with the top wall of said base panel.

5. The parts for a heat sink as claimed in claim 1, further comprising at least one heat pipe for passing through said radiation fins, each said heat pip having a bottom end mounted in a bottom side of said base panel in a flush manner.

* * * * *